US00PP14971P2

(12) United States Plant Patent
Olesen et al.

(10) Patent No.: US PP14,971 P2
(45) Date of Patent: Jun. 29, 2004

(54) MINIATURE ROSE PLANT NAMED 'POULHI009'

(50) Latin Name: *Rosa hybrida*
Varietal Denomination: POULhi009

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/267,976

(22) Filed: Oct. 8, 2002

(51) Int. Cl.[7] ..... A01H 5/00
(52) U.S. Cl. ..... Plt./118
(58) Field of Search ..... Plt./118, 125, 116

*Primary Examiner*—Anne Marie Grunberg
*Assistant Examiner*—June Hwu

(57) ABSTRACT

A new miniature rose plant which has abundant, yellow flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Classification: Botanical: *Rosa hybrida* 'POULhi009'. Commercial: miniature rose.

SUMMARY OF THE INVENTION

The present invention constitutes a new and distinct variety of miniature rose plant which originated from a controlled crossing between 'POULsabel', described and illustrated in U.S. Plant patent application Ser. No. 10/136,451 dated Apr. 29, 2002, which is a continuation of 09/607,333, dated Jun. 30, 2000, and 'KORstoffein' described and illustrated in U.S. Plant Pat. No. 11,242, issued on Feb. 22, 2000. The two parents were crossed and the resulting seeds were planted in a controlled environment. The new variety is named 'POULhi009'.

The new rose may be distinguished from its seed parent, 'POULsabel' by the following combination of characteristics:

1. The flowers of 'POULsabel' are dark red, whereas those of 'POULhi009' are yellow.
2. 'POULsabel' has 25 to 30 petals, while 'POULhi009' has 40 to 45 petals.

The new variety may be distinguished from its pollen parent, 'KORstoffein' by the following combination of characteristics:

1. The flowers of 'KORstoffein' are peach-colored, while those of 'POULhi009' are yellow.
2. The leaves of 'KORstoffein' are matte, whereas those of 'POULhi009' are glossy.

The objective of the hybridization of this rose variety for commercial culture was to create a new and distinct variety with unique qualities, such as:

1. Uniform and abundant flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type and distinguish 'POULhi009' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULhi009' was selected by the inventors as a single plant from the progeny of the hybridization in May of 1999.

Asexual reproduction of 'POULhi009' by cuttings and traditional budding was first done by L. Pernille and Mogens N. Olesen in their nursery in Fredensborg, Denmark in October of 1999. This initial and other subsequent propagations conducted in controlled environments have demonstrated that the characteristics of 'POULhi009' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULhi009'. Specifically illustrated in SHEET 1:

1. Stem showing opened flowers, branching and the attachment of leaves, buds, and peduncles;

2. Flower bud, partially opened bud, and open bloom;

3. Flower petals, detached;

4. Sepals, receptacle, and pedicel;

5. Two bare stems exhibiting thorns;

6. Leaves.

DETAILED DESCRIPTION OF THE VARIETY

The following is a description of 'POULhi009', as observed in its growth in 3 year old budded plants in a field nursery in Jackson County, Oreg. Color references are made using The Royal Horticultural Society (London, England) Colour Chart, 1995, except where common terms of color are used.

For a comparison, several physical characteristics of the rose variety 'POULra001', a rose variety from the same inventors described and illustrated in U.S. Plant Pat. No. 13,487 dated Jan. 21, 2003 are compared to 'POULhi009' in Chart 1.

CHART 1

| | 'POULhi009' | 'POULra001' |
|---|---|---|
| Petal count | 40 to 45 petals | 50–60 petals |
| Color, upper petal surface | Yellow Group 10D. | Red Group 48C. |
| Color, lower petal surface | Yellow-Orange Group 18B. | Red Group 52D. |

Parents: 'POULsabel'×'KORstoffein'

FLOWER AND FLOWER BUD

Blooming habit: Recurrent/continuous.

Flower bud:

*Size.*—Upon opening, 20 mm in length from base of receptacle to end of bud.

*Bud form.*—Pointed ovoid.

*Bud color.*—As sepals unfold, upper surface is Yellow-Orange Group 18B; lower surface is Yellow-Orange Group 18B. At ¼ opening, upper surface of sepals is yellow-orange Group 18B; lower surface is Yellow-Orange Group 18B.

*Sepals.*—Upper surface margins are green Group 137A; interior is Yellow-Green Group 144B. Strong foliaceous appendages on three of the five sepals. Surfaces of sepals are moderately pubescent. Stipitate glands are present on margins and undersides of sepals. Shape: Sepal apex is cirrose. Base is flat at union with peduncle. Size: 22 to 30 mm long×5 to 7 mm wide.

*Receptacle.*—Surface: Smooth. Shape: Narrow funnel. Size: 4 mm (h)×4 mm (w). Color: Yellow-Green Group 144A.

*Peduncle.*—Surface: Many stipitate glands present. Length: 40 to 50 average length. Color: Yellow-Green Group 144A and B. On plants grown under high light conditions, peduncle may exhibit intonations of Greyed-Purple Group 185A. Strength: Somewhat strong.

*Borne.*—Singly or in small clusters of up to 3.

*Anthocyanin.*—Greyed-Purple Group 185A.

Flower bloom:

*Fragrance.*—Light.

*Duration.*—As a pot plant, flowers last from 8 to 10 days.

*Size.*—Large for a 12 cm pot rose. Average flower diameter is 60 mm when open.

*Form.*—Shape of flower when viewed from the side: Upon opening, upper part: Flattend convex. Upon opening, lower part: Concave. Open flower, upper part: Flattened convex. Open flower, lower part: Concave.

*Petalage.*—Average range: 40 to 45 petals under normal conditions with 1 to 3 petaloids.

Color:

*Upon opening, petals.*—Outermost petals: Outer Side: Yellow-Orange Group 18C. Inner Side: Yellow Group 10D. Innermost petals: Outer Side: Yellow-Orange Group 18B. Inner Side: Blend of Yellow-Orange Group 18A and Yellow Group 13C.

*Upon opening, basal petal spots.*—Outermost petals: Outer Side: Yellow Group 6C. Inner Side: Yellow-Group 6A. Innermost petals: Outer Side: Yellow-Group 6A. Inner Side: Yellow-Group 6A.

*After opening, petals.*—Outermost petals: Outer Side: Yellow Group 4D. Inner Side: Yellow Group 4D. Innermost petals: Outer Side: Yellow Group 4C. Inner Side: Yellow Group 4C.

*After opening, basal petal spots.*—Outermost petals: Outer Side: Yellow Group 4A. Inner Side: Yellow Group 4A. Innermost petals: Outer Side: Yellow Group 4A. Inner Side: Yellow Group 4A.

General tonality: on open flower Yellow Group 6A. No change in the general tonality at the end of the $6^{th}$ day. Afterwards, general tonality is yellow Group 4D.

Petals:

*Petal reflex.*—Petals reflex somewhat.

*Petal edge.*—Petal edge is entire with occasional point in center of margin.

*Shape.*—Apex and base are rounded.

*Size.*—25 mm in length by 22 mm wide.

*Texture.*—Smooth.

*Petaloids.*—Quantity: 1 to 3. Size: 8 mm long, 5 mm wide. Color: Yellow-Orange Group 18A on upper surface, Yellow-Orange Group 18A and B on lower surface.

*Thickness.*—Average.

*Arrangement.*—Formal.

Reproductive organs:

*Pistils.*—Length: 10 to 12 mm long. Quantity: 30 to 35.

*Pollen.*—Color: None observed.

*Anthers.*—Size: 2 mm long. Color: Margins are Yellow-Orange Group 22A. Interior is red Group 38B. Quantity: 55 to 60.

*Filaments.*—Color: Green-Yellow Group 1A. Length: 4 mm.

*Stigma.*—Superior in location to anthers. Color: Yellow-Green Group 154C.

*Styles.*—Color: Red Group 46A.

*Seed formation.*—Hips: None observed.

PLANT

Plant growth: Vigorous, compact, upright to bushy. When grown as a 12 cm pot plant, the average height of the plant itself is 20 cm and the average width is 25 to 28 cm.

Stems:

*Color.*—Young wood: Yellow-Green Group 146D. Older wood: Yellow-Green Group 146A.

*Prickles.*—Incidence: 8 Thorns per 10 cm of stem. Size: Average length: 7 to 8 mm. Color: Greyed-Purple Group 185A. Shape: Linear with downward hook.

*Surface.*—Young wood: Smooth. Older wood: Smooth.

Plant foliage: Normal number of leaflets on leaves in middle of the stem: 5 to 7 leaflets.

*Leaf size.*—110 mm (l)×75 mm (w).

*Quantity.*—Abundant.

*Color.*—Upper Leaf Surface: Green Group 137A. Lower Leaf Surface: Yellow-Green Group 147C. Juvenile foliage: Upper Leaf Surface: Green Group 138A. Lower Leaf Surface: Yellow-Green Group 147C. Anthocyanin intonation: Location: Stipules, leaflet margins, rachis, petiole.

Plant leaves and leaflets:

*Stipules.*—Size: 15 mm long. Color: Margins are Green Group 138A. Interior is Yellow-Green Group 144C. Stipitate glands: Present on stipule edges. Anthocyanin: Greyed-Purple Group 185A.

*Petiole.*—Length: 12 to 15 mm. Color: Yellow-Green Group 144A. Underneath: Many tiny thorns present.

Stipitate glands: Present on petiole edges. Anthocyanin: Greyed-Purple Group 185A.

*Rachis.*—Color: Yellow-Green Group 144A. Underneath: Many tiny thorns present. Stipitate glands: Present on petiole edges. Anthocyanin: Greyed-Purple Group 185A.

*Leaflet.*—Edge: Finely serrated. Shape: Broadly ovate. Apex is cuspidate. Base is rounded. Texture: Leathery and moderately glossy. Arrangement: Odd pinnate. Venation: Reticulate.

Disease resistance: Average resistance to mildew, black spot, and Botrytis under normal growing conditions in Jackson County, Oreg.

Cold hardiness: 'POULhi009' has been found to be resistant to damage from cold, heat and drought damage in USDA zones 5 and 6.

What is claimed is:

1. A new and distinct variety of rose plant of the miniature class, substantially as herein illustrated and described as a distinct and novel rose variety due to its abundant, yellow flowers, vigorous growth, compact habit, suitability for production from softwood cuttings in pots, and durable flowers and foliage which make the variety suitable for distribution in the floral industry.

* * * * *

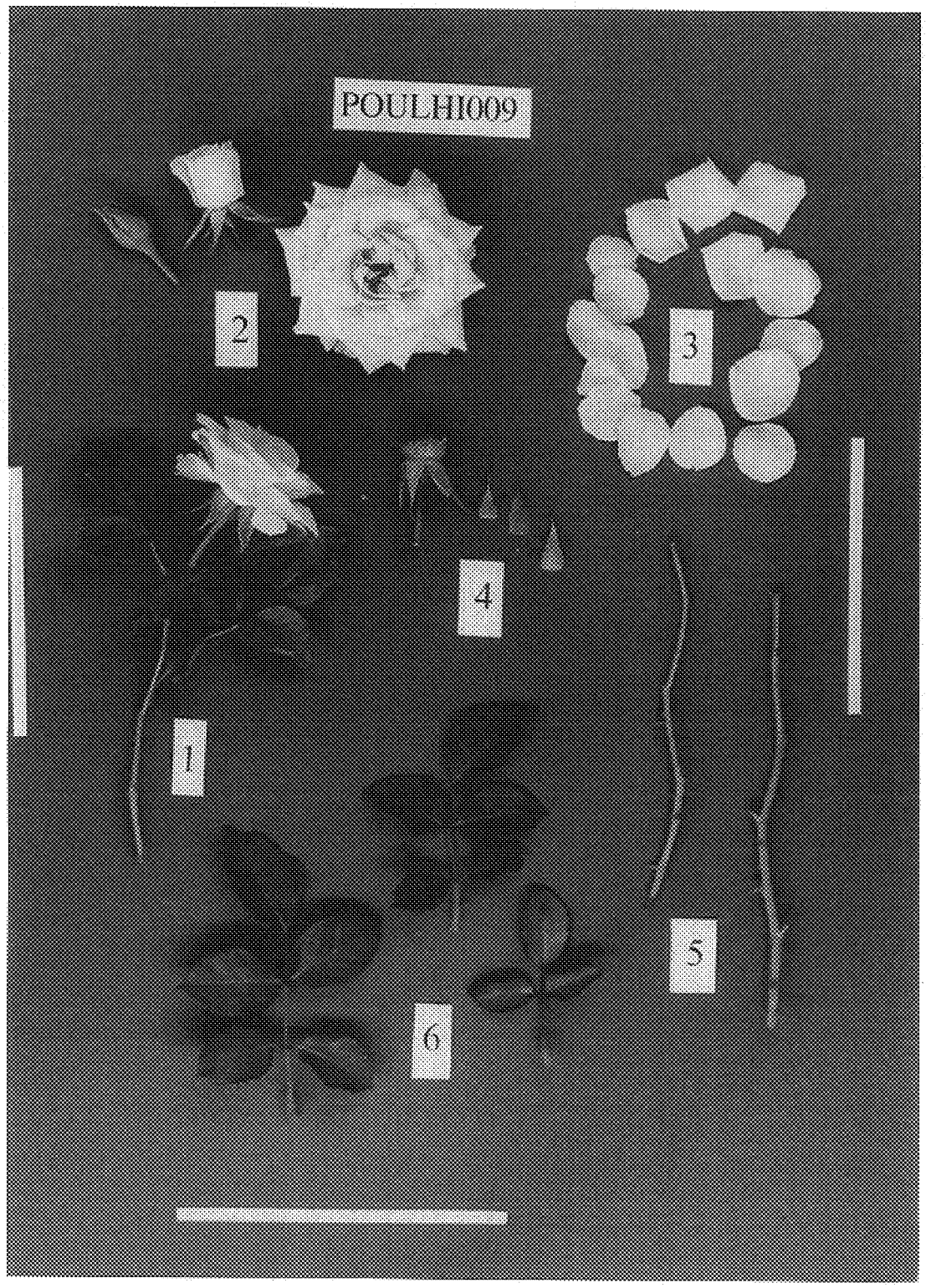
POULH1009
1
2
3
4
5
6
7